US012796924B2

(12) United States Patent
Ho et al.

(10) Patent No.: US 12,796,924 B2
(45) Date of Patent: Nov. 17, 2026

(54) INTRAOCULAR PRESSURE DETECTION DEVICE AND GLASSES WITH INTRAOCULAR PRESSURE DETECTION FUNCTION

(71) Applicants: Asphetek Solution (Chengdu) Ltd., Chengdu (CN); Asphetek Solution Inc., Hsinchu (TW)

(72) Inventors: Chung-Chiao Ho, Hsinchu (TW); Yu-Pi Kuo, Hsinchu (TW); Chung-Wu Liu, Hsinchu (TW)

(73) Assignees: Asphetek Solution (Chengdu) Ltd., Chengdu (CN); Asphetek Solution Inc., Hsinchu (TW)

( * ) Notice: Subject to any disclaimer, the term of this patent is extended or adjusted under 35 U.S.C. 154(b) by 466 days.

(21) Appl. No.: 18/378,099

(22) Filed: Oct. 9, 2023

(65) Prior Publication Data

US 2025/0049318 A1 Feb. 13, 2025

(30) Foreign Application Priority Data

Aug. 7, 2023 (CN) ......................... 202322109322.7

(51) Int. Cl.
*A61B 3/16* (2006.01)

(52) U.S. Cl.
CPC .................................... *A61B 3/165* (2013.01)

(58) Field of Classification Search
None
See application file for complete search history.

(56) References Cited

U.S. PATENT DOCUMENTS

| | | | | |
|---|---|---|---|---|
| 2003/0088169 | A1 * | 5/2003 | Percival | A61B 3/0058 600/399 |
| 2004/0183998 | A1 * | 9/2004 | Luce | A61B 3/1005 351/212 |
| 2004/0193033 | A1 * | 9/2004 | Badehi | A61B 3/165 600/402 |
| 2014/0114145 | A1 * | 4/2014 | Wang | A61B 3/165 600/301 |
| 2017/0000345 | A1 * | 1/2017 | Samec | G02B 27/0172 |
| 2017/0181626 | A1 * | 6/2017 | Shau | A61B 3/14 |
| 2022/0061661 | A1 * | 3/2022 | Obama | A61B 3/16 |

* cited by examiner

*Primary Examiner* — Etsub D Berhanu
(74) *Attorney, Agent, or Firm* — ScienBiziP, P.C.

(57) ABSTRACT

The present application provides intraocular pressure detection device and glasses with intraocular pressure detection function. The intraocular pressure detection device includes a light-emitting assembly, an optical signal receiving assembly, and a processor. The light-emitting assembly is arranged toward an eyeball, and is configured to emit a first ray to the eyeball. The first ray is partially absorbed by the eyeball to form a second ray. The optical signal receiving assembly is located on one side of the light-emitting assembly, and is set toward the eyeball for receiving a third ray, and the third ray is formed after the second ray is reflected by the eyeball, and the optical signal receiving assembly is used to convert the received third ray into a detection signal. The processor is electrically connected to the optical signal receiving assembly, and configured for receiving the detection signal and converting the detection signal into intraocular pressure data.

15 Claims, 4 Drawing Sheets

INTRAOCULAR PRESSURE DETECTION DEVICE AND GLASSES WITH INTRAOCULAR PRESSURE DETECTION FUNCTION

FIELD

The present application relates to the technical field of intraocular pressure detection, and in particular to an intraocular pressure detection device and glasses with intraocular pressure detection function.

BACKGROUND

Most of the existing intraocular pressure detection equipment is attached to surface of an eyeball with flexible materials. When a curvature of the eyeball changes, the flexible material will also deform accordingly, and then detect the current intraocular pressure of the eyeball according to the deformation of the flexible material. This direct detection method requires a flexible material to be attached to the surface of the eyeball for a long time, which is more inconvenient during detection and can easily cause discomfort.

Those skilled in the art need to consider how to solve the above problems, provide an intraocular pressure detection device that is convenient for detection and less likely to cause discomfort, and glasses with an intraocular pressure detection function.

SUMMARY

An embodiment of the present application provides an intraocular pressure detection device, including a light-emitting assembly, an optical signal receiving assembly and a processor. The light-emitting assembly is arranged toward an eyeball, and the light-emitting assembly is configured to emit a first ray to the eyeball. The first ray is partially absorbed by the eyeball to form a second ray. The optical signal receiving assembly is arranged at a side of the light-emitting assembly, and the optical signal receiving assembly is disposed toward the eyeball for receiving a third ray. The second ray is reflected by the eyeball to form the third ray. The optical signal receiving assembly is configured to convert the received third ray into a detection signal. The processor is electrically connected to the optical signal receiving assembly. The processor is configured to receive the detection signal and convert the detection signal into intraocular pressure data.

The intraocular pressure detection device of the present application emits the first ray of a specific wavelength band to the eyeball through the light-emitting assembly. Part of the first ray is absorbed by the eyeball, and remaining light in the first ray is reflected by the eyeball and then transmitted to the optical signal receiving assembly. The optical signal receiving assembly converts the received light into a detection signal. When an intraocular pressure of the eyeball is different, the absorption amount of the first ray by the eyeball is also different, resulting in the different amount of light received by the optical signal receiving assembly, and the converted detection signal is also different. The different detection signal is compared with a pre-measured standard signal to obtain a current intraocular pressure. The intraocular pressure detection device of the present application adopts a non-contact detection method, the non-contact detection method is simple, and it does not need to be in contact with the eyeball during detection, and will not cause discomfort to the eyeball.

DETAILED DESCRIPTION

In order to make the above-mentioned objects, features and advantages of the present application more obvious, a detailed description of specific embodiments of the present application will be described in detail with reference to the accompanying drawings. A number of details are set forth in the following description so as to fully understand the present application. However, the present application can be implemented in many other ways different from those described herein, and those skilled in the art can make similar improvements without violating the contents of the present application. Therefore, the present application is not to be considered as limiting the scope of the embodiments described herein.

Several definitions that apply throughout this disclosure will now be presented.

The term "coupled" is defined as coupled, whether directly or indirectly through intervening components, and is not necessarily limited to physical connections. The connection may be such that the objects are permanently coupled or releasably coupled. The term "substantially" is defined to be essentially conforming to the particular dimension, shape, or other feature that the term modifies, such that the component need not have that exact feature. The term "comprising," when utilized, means "including, but not necessarily limited to;" it specifically indicates open-ended inclusion or membership in the so-described combination, group, series, and the like.

Unless otherwise defined, all technical and scientific terms used herein have the same meaning as commonly understood by one skilled in the art. The terms used in a specification of the present application herein are only for describing specific embodiments and are not intended to limit the present application. The terms "and/or" used herein includes any and all combinations of one or more of associated listed items.

Figure 1:
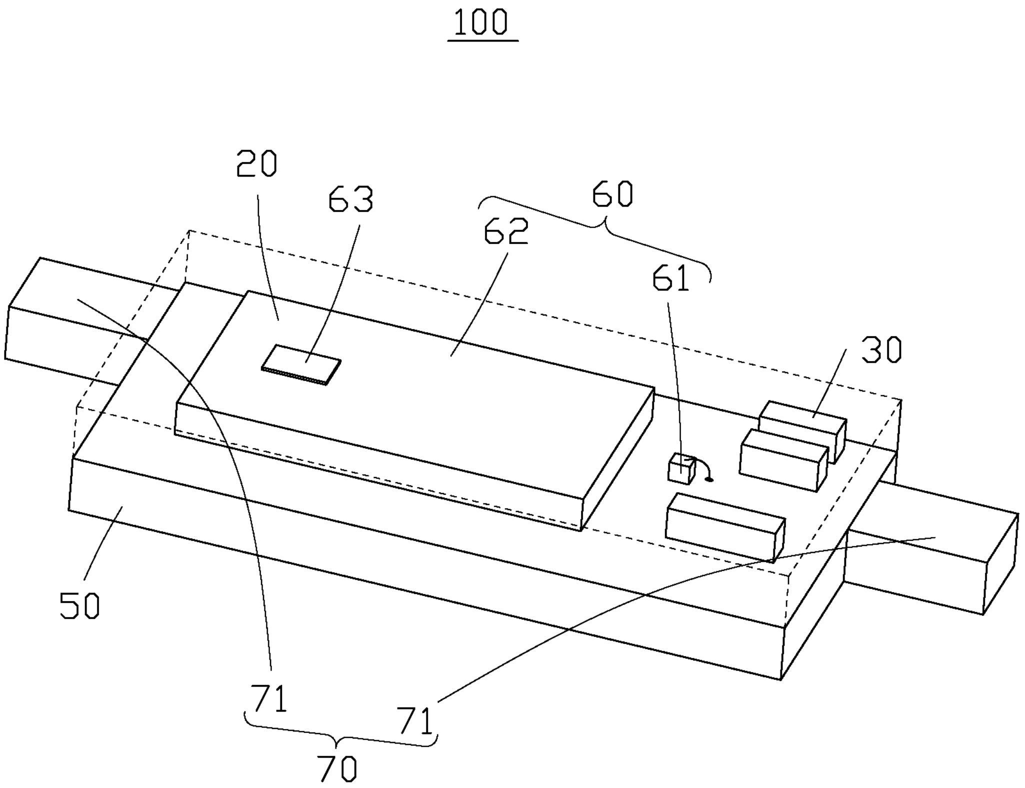
FIG. 1 is a schematic view of an intraocular pressure detection device according to one embodiment of the present disclosure.
Figure 2:
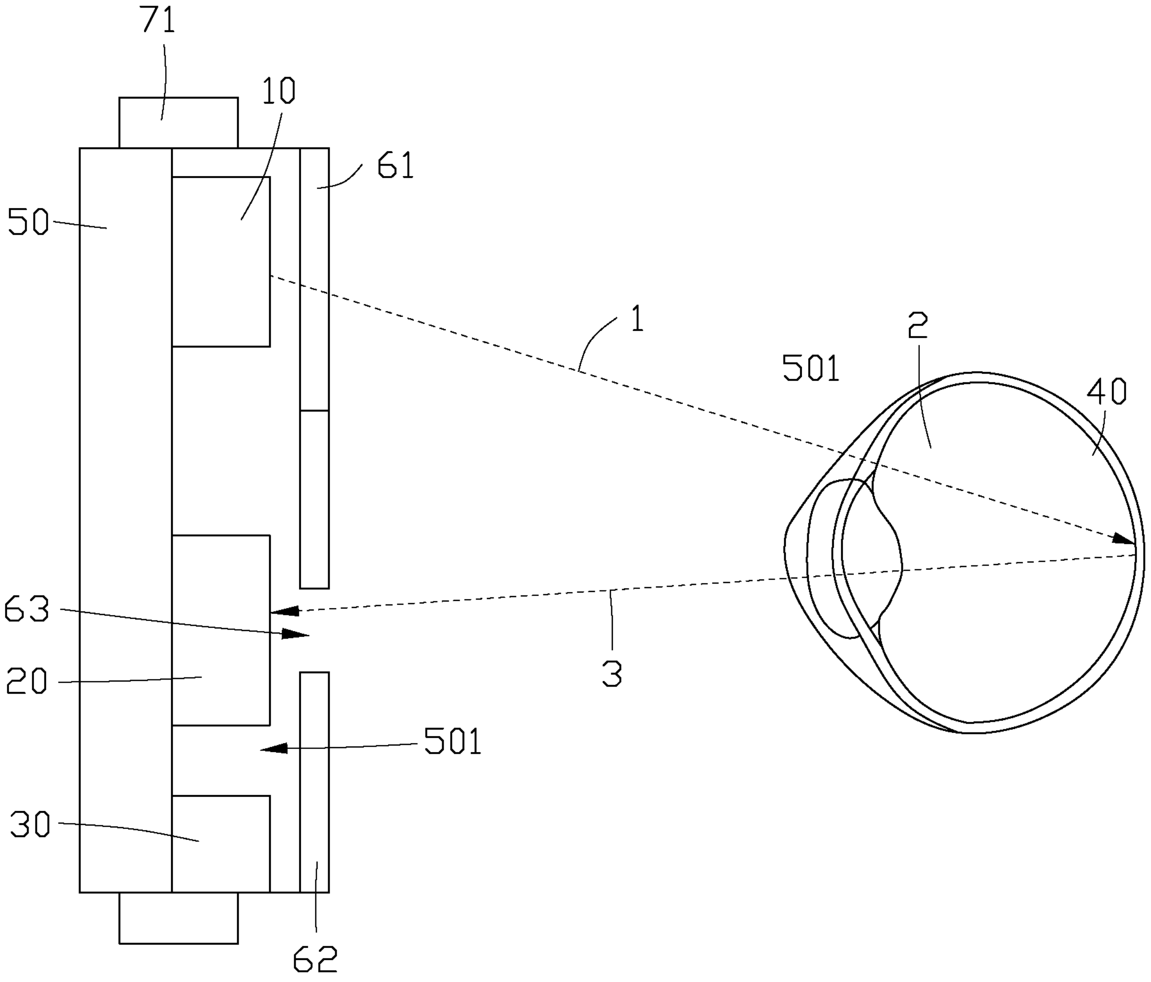
FIG. 2 is a working diagram of the intraocular pressure detection device according to one embodiment of the present disclosure.
Figure 3:
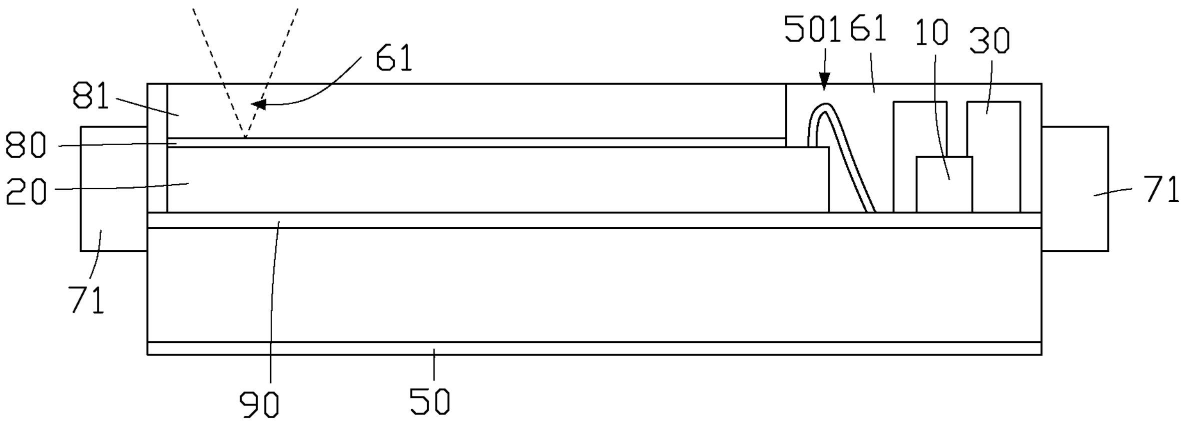
FIG. 3 is a schematic view of an internal structure of the intraocular pressure detection device according to one embodiment of the present disclosure.

Referring to FIG. 1, FIG. 2, and FIG. 3, an intraocular pressure detection device 100 is disclosed in one embodiment. The intraocular pressure detection device 100 includes a light-emitting assembly 10, an optical signal receiving assembly 20, and a processor 30.

The light-emitting assembly 10 can be a light-emitting diode lamp, and the light-emitting assembly 10 is arranged toward an eyeball 40. The light-emitting assembly 10 is configured to emit a first ray 1 to the eyeball 40. A wavelength of the first ray 1 is 300 nm to 1100 nm, which includes green light, yellow light, infrared light, etc. When green light and yellow light are emitted into the eyeball 40, they will be absorbed by hemoglobin in blood vessels in the eyeball 40, while infrared light is difficult to be absorbed by hemoglobin. The green light and yellow light in the first ray 1 are absorbed by hemoglobin to form the second ray 2. Most of the light in the second ray 2 is infrared light. The second ray 2 passes through the blood vessels and is reflected by a back wall of the eyeball 40, thus the second ray 2 is reflected to form a third ray 3.

The optical signal receiving assembly 20 is arranged at a side of the light-emitting assembly 10 and is disposed toward the eyeball 40 for receiving the third ray 3. Positions of the light-emitting assembly 10, the optical signal receiving assembly 20, and the eyeball 40 can be adjusted, to ensure that the optical signal receiving assembly 20 can receive the third ray 3. The optical signal receiving assembly 20 can be a light sensor, which can convert an optical signal into an electrical signal. The optical signal receiving assembly 20 is configured to convert the received third ray 3 into a detection signal. A value of the detection signal varies with an energy of the third ray 3 received by the optical signal receiving assembly 20.

Compared with a normal level of an intraocular pressure in the eyeball 40, when the intraocular pressure in the eyeball 40 increases, the blood vessels in the eyeball 40 will constrict, the hemoglobin content in the blood vessels will decrease, and the absorption of green light and yellow light in the first ray 1 will decrease, so that light intensity of the second ray 2 will increase accordingly. Therefore, when compared with the intraocular pressure of the eyeball 40 at a normal level, the light intensity of the third ray 3 received by the optical signal receiving assembly 20 will increase, and the value of the detection signal converted by the third ray 3 will become larger. Therefore, the magnitude of the internal pressure of the eyeball 40 can be reflected by the numerical magnitude of the detection signal.

The processor 30 is electrically connected to the optical signal receiving assembly 20. The processor 30 is configured for receiving detection signals and converting the detection signals into intraocular pressure data. The processor 30 is preset with standard signals and standard intraocular pressure data. The standard signals and standard intraocular pressure data are obtained in a standard test. A test environment of the standard test is same as a detection environment of the intraocular pressure detection device 100. For example, positions of the light-emitting assembly 10 and the optical signal receiving assembly 20, and the eyeball 40 shall be consistent. The wavelength band and light intensity of the first ray 1 remain consistent, an incident angle of the first ray 1 remains consistent, and so on. When an intraocular pressure detection is performed by using the intraocular pressure detection device 100 of the present application, it is necessary to ensure that the detection environment is the same as that in the standard test to ensure the accuracy of the detection results.

When conducting the standard test, a test principle of the present application is applied in the standard test for measurement. The light-emitting assembly 10 emits ray with a wavelength range of 300 nm to 1100 nm to the eyeballs 40 with different intraocular pressures, and the optical signal receiving assembly 20 receives standard signals corresponding different intraocular pressures, and inputs standard signals and standard intraocular pressure data corresponding to the standard signals to the processor 30 for storage. Therefore, when the intraocular pressure detection device 100 is making a detection, the processor 30 can retrieve standard intraocular pressure data according to the detection signal produced by the optical signal receiving assembly 20. The corresponding standard intraocular pressure data is the intraocular pressure of the currently detected eyeball 40. Furthermore, the processor 30 can also be electrically connected with an alarm component (not shown in figures). When the intraocular pressure of the eyeball 40 obtained by the processor 30 exceeds a preset threshold value, the processor 30 controls the alarm component to send out an alarm signal. The alarm component can include flashing lights or voice reminders.

It should be noted that, in order to ensure that the intraocular pressure detection device 100 of the present application can be used in same environment as the test environment of the standard test, the intraocular pressure detection device 100 is also provided with a position detection component 70. The position detection assembly 70 includes a plurality of laser distance measuring devices 71. The plurality of laser distance measuring devices 71 is configured to detect the position of the intraocular pressure detection device 100 relative to the eyeball 40, ensuring that an optical path of the intraocular pressure detection device 100 during detection is consistent with an optical path of the standard test.

In this way, the intraocular pressure detection device 100 of the present application emits the first ray 1 of a specific wavelength band to the eyeball 40 through the light-emitting assembly 10. Part of the light in the first ray 1 is absorbed by the eyeball 40, and the remaining light in the first ray 1 is reflected and transmitted to the optical signal receiving assembly 20. The optical signal receiving assembly 20 converts the received light into a detection signal. When the intraocular pressure of the eyeball 40 is changed, the amount of absorption of the first ray 1 by the eyeball 40 is also changed, resulting in a different amount of light received by the optical signal receiving assembly 20 and a different detection signal converted from the received light. Therefore, the different detection signal can be compared with pre-measured standard signals to get the current intraocular pressure. The intraocular pressure detection device 100 of the present application adopts a non-contact detection method, the non-contact detection method is simple, and during detection, the intraocular pressure detection device 100 does not need to contact with the eyeball 40 and will not cause discomfort to the eyeball 40.

Please refer to FIGS. 1 to 3, in one embodiment, the intraocular pressure detection device 100 further includes a housing 50 and a cover plate 60. The housing 50 can be a square, or a columnar structure, etc. One end of the housing 50 facing the eyeball 40 is provided with a mounting groove 501. The light-emitting assembly 10 and the optical signal receiving assembly 20 are received in the mounting groove 501, and the light-emitting assembly 10 and the optical signal receiving assembly 20 are spaced apart. The cover plate 60 covers the one end of the housing 50 facing the eyeball 40, and the cover plate 60 is configured to close the mounting groove 501. The cover plate 60 is detachably connected to the housing 50 by means of screw connection or clamping, so that the position of the light-emitting component 10 and the optical signal receiving assembly 20 in the mounting groove 501 can be adjusted after the cover plate 60 is removed.

There are two laser distance measuring devices 71, and the two laser distance measuring devices 71 are respectively arranged on opposite sides of the housing 50. The two laser distance measuring devices 71 are set towards the eyeball 40 to emit distance detection light to the eyeball 40. The distance of two laser distance measuring devices 71 relative to eyeball 40 is measured to locate the position of the intraocular pressure detection device 100 relative to eyeball 40.

Please continue to refer to FIG. 1 to FIG. 3, in one embodiment, the cover plate 60 includes a light-transmitting portion 61 and a light-shielding portion 62. The light-transmitting portion 61 and the light-shielding portion 62 can be connected in one piece, or detachably connected to each other. The light-transmitting portion 61 corresponds to the light-emitting assembly 10 and is located on the optical path of the first ray 1. The light-transmitting portion 61 is made of a transparent material such as glass, so that the first ray 1 emitted by the light-emitting component 10 can pass through the light-transmitting portion 61 and be projected to the eyeball 40. The light-shielding portion 62 corresponds to the optical signal receiving assembly 20. The light-shielding portion 62 can be made of an opaque material for blocking light outside the housing 50 from projecting to the optical signal receiving assembly 20.

In other embodiments, a surface of the light-shielding portion 62 close to the optical signal receiving assembly 20 can be coated with black ink or pasted with black tape. The black ink and black tape are configured to block light. In this case, the light-shielding portion 62 and the light-transmitting portion 61 can be integrally formed by using a same material.

In particular, the light-shielding portion 62 is provided with a light-transmitting port 63, and the light-transmitting port 63 passes through the light-shielding portion 62 and communicates with the mounting groove 501. The light-transmitting opening 63 is disposed toward the eyeball 40 and allows the third ray 3 to pass through, so that the third ray 3 can be received by the optical signal receiving assembly 20 after passing through the light-transmitting opening 63.

A diameter of the light-transmitting opening 63 should be set to 300 μm~1200 μm, to ensure that the third ray 3 can pass through the light-transmitting opening 63 as much as possible, and the light emitted by other light sources outside the housing 50 is blocked by the light-shielding portion 62 as much as possible, improving the accuracy of detection.

In order to prevent light emitted by other light sources outside the housing 50 from entering the mounting groove 501, the housing 50 can be made of light-shielding material.

Please continue to refer to FIG. 1 to FIG. 3, in an embodiment, the intraocular pressure detection device 100 further includes an optical filter 80. The optical filter 80 is received in the mounting groove 501 and is arranged between the light-shielding portion 62 and the optical signal receiving assembly 20. The optical filter 80 is configured to prevent light other than green light, yellow light, and infrared light in the third ray 3 from entering the optical signal receiving assembly 20. A size of the optical filter 80 should be larger than a size of the light-transmission port 63 to ensure that the third ray entering from the light transmission port 63 can pass through the filter 80, improving accuracy of detection.

In particular, the optical filter 80 can be attached to an end of the optical signal receiving assembly 20 facing the eyeball 40, to improve the filtering effect of the optical filter 80.

Please continue to refer to FIG. 1 to FIG. 3, in an embodiment, the intraocular pressure detection device 100 further includes a shim 81, and the shim 81 is sandwiched between the filter 80 and the light shielding portion 62. The shim 81 is in a planar structure. A top side of the shim 81 abuts against the light-shielding portion 62, and a bottom side of the shim 81 abuts against the optical filter 80. The optical filter 80 is pressed against the optical signal receiving assembly 20 through the shim 81, so that stability of the optical filter 80 and the optical signal receiving assembly 20 can be improved. The shim 81 can be made of light-transmitting material to let the third ray 3 can completely pass through the shim 81 and then enter the optical filter 80.

In one embodiment, the shim 81 can be made of elastic material. The shim 81 elastically contacts the optical filter 80, which can prevent the optical filter 80 and the optical signal receiving assembly 20 from being damaged in the case of violent shaking.

Please continue to refer to FIG. 1 to FIG. 3, in an embodiment, the intraocular pressure detection device 100 further includes a circuit board 90. The circuit board 90 is received in the mounting groove 501. The circuit board 90 is arranged under the optical signal receiving assembly 20 and is horizontally fixed in the housing 50. The optical signal receiving assembly 20 abuts against the circuit board 90. Positions of the optical filter 80 and the optical signal receiving assembly 20 are fixed through the shim 81 and the circuit board 90 to prevent them from shifting. The light-emitting assembly 10, the optical signal receiving assembly 20, and the processor 30 are electrically connected to the circuit board 90. In addition, the light-emitting assembly 10 and the optical signal receiving assembly 20 are arranged at a same side of the circuit board 90, and the light-emitting component 10 is fixed on the circuit board 90. Integrating the light-emitting component 10 and the optical signal receiving assembly 20 on the circuit board 90 can improve the compactness of the structure and facilitate the miniaturization of the device.

Figure 4:
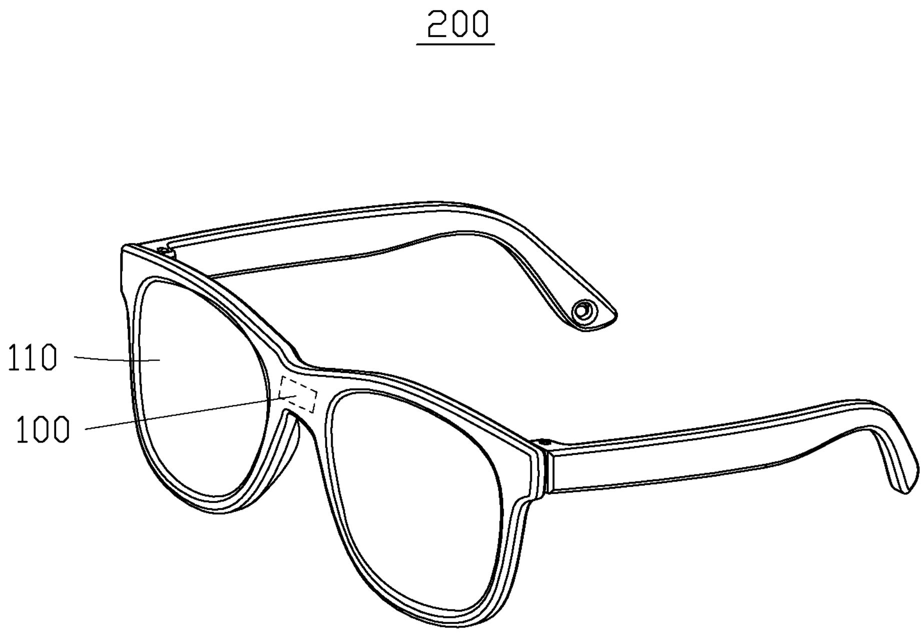
FIG. 4 is a schematic view of a pair of glasses with intraocular pressure detection function.

Referring to FIG. 4, an embodiment of the present application also provides a pair of glasses 200 with an intraocular pressure detection function. The pair of glasses 200 includes a glasses frame 110 and the above-mentioned intraocular pressure detection device 100. The intraocular pressure detection device 100 is installed on the glasses frame 110. When a user wears the glasses, the intraocular pressure of the user can be detected in real time by the intraocular pressure detection device 100.

The intraocular pressure detection device 100 can be installed on a nose edge of the glasses frame 110, or can be installed on a side of the spectacle frame 110. A specific installation position of the intraocular pressure detection device 100 can be adjusted according to actual design requirements.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:

1. An intraocular pressure detection device, comprising:

a light-emitting assembly, wherein the light-emitting assembly is arranged toward an eyeball, and the light-emitting assembly is configured to emit a first ray to the eyeball, the first ray is partially absorbed by the eyeball to form a second ray;

an optical signal receiving assembly, wherein the optical signal receiving assembly is arranged at a side of the light-emitting assembly, and the optical signal receiving assembly is disposed toward the eyeball for receiving a third ray, the second ray is reflected by the eyeball to form the third ray, and the optical signal receiving assembly is configured to convert the received third ray into a detection signal;

a processor, wherein the processor is electrically connected to the optical signal receiving assembly, and the processor receives the detection signal and converts the detection signal into intraocular pressure data; and a housing and a cover plate, wherein the housing defines a mounting groove at one end facing the eyeball, the light-emitting assembly and the optical signal receiving assembly are received in the mounting groove, and the cover plate is on the one end of the housing facing the eyeball to cover at least part of the mounting groove; and wherein the cover plate comprises a light-transmitting portion and a light-shielding portion, the light-transmitting portion is located on a path of the first ray, the first ray passes the light-transmitting portion, and the light-shielding portion blocks external light projected to the optical signal receiving assembly.

2. The intraocular pressure detection device as claimed in claim 1, wherein a wavelength of the first ray is 300 nm to 1100 nm.

3. The intraocular pressure detection device as claimed in claim 1, wherein the light-shielding portion defines a light-transmitting port, the light-transmitting port faces the eyeball, and the third ray passes the light-transmitting port.

4. The intraocular pressure detection device as claimed in claim 1, further comprising an optical filter, wherein the optical filter is arranged between the optical signal receiving assembly and the light-shielding portion, and the optical filter prevents non-infrared light in the third ray from entering the optical signal receiving assembly.

5. The intraocular pressure detection device as claimed in claim 4, further comprising a shim, wherein the shim is positioned between the optical filter and the light-shielding portion, and the shim is made of a transparent material.

6. The intraocular pressure detection device as claimed in claim 1, wherein a surface of an end of the light-shielding portion near the optical signal receiving assembly is coated with ink, and the ink is configured for blocking light.

7. The intraocular pressure detection device as claimed in claim 1, further comprising a circuit board, wherein the circuit board is received in the mounting groove, and the light-emitting assembly, the optical signal receiving assembly, and the processor are electrically connected to the circuit board.

8. A pair of glasses with intraocular pressure detection function, comprising:

a glasses frame; and an intraocular pressure detection device arranged in the glasses frame, wherein the intraocular pressure detection device comprises:

a light-emitting assembly, wherein the light-emitting assembly is arranged toward an eyeball, and the light-emitting assembly is configured to emit a first ray to the eyeball, wherein the first ray is partially absorbed by the eyeball to form a second ray, an optical signal receiving assembly, wherein the optical signal receiving assembly is arranged at a side of the light-emitting assembly, and the optical signal receiving assembly is disposed toward the eyeball for receiving a third ray, the second ray is reflected by the eyeball to form the third ray, and the optical signal receiving assembly is configured to convert the received third ray into a detection signal, a processor, wherein the processor is electrically connected to the optical signal receiving assembly, and the processor receives the detection signal and converts the detection signal into intraocular pressure data; and a housing and a cover plate, wherein the housing defines a mounting groove at one end facing the eyeball, the light-emitting assembly and the optical signal receiving assembly are received in the mounting groove, and the cover plate is on the one end of the housing facing the eyeball to cover at least part of the mounting groove.

9. The pair of glasses with intraocular pressure detection function as claimed in claim 8, wherein a wavelength of the first ray is 300 nm to 1100 nm.

10. The pair of glasses with intraocular pressure detection function as claimed in claim 8, wherein the cover plate comprises a light-transmitting portion and a light-shielding portion, the light-transmitting portion is located on a path of the first ray, the first ray passes the light-transmitting portion, and the light-shielding portion blocks external light projected to the optical signal receiving assembly.

11. The pair of glasses with intraocular pressure detection function as claimed in claim 10, wherein the light-shielding portion defines a light-transmitting port, the light-transmitting port faces the eyeball, and the third ray passes the light-transmitting port.

12. The pair of glasses with intraocular pressure detection function as claimed in claim 10, wherein the intraocular pressure detection device further comprises an optical filter, the optical filter is arranged between the optical signal receiving assembly and the light-shielding portion, and the optical filter prevents non-infrared light in the third ray from entering the optical signal receiving assembly.

13. The pair of glasses with intraocular pressure detection function as claimed in claim 12, wherein the intraocular pressure detection device further comprises a shim, the shim is positioned between the optical filter and the light-shielding portion, and the shim is made of a transparent material.

14. The pair of glasses with intraocular pressure detection function as claimed in claim 10, wherein a surface of an end of the light-shielding portion near the optical signal receiving assembly is coated with ink, and the ink is configured for blocking light.

15. The pair of glasses with intraocular pressure detection function as claimed in claim 8, wherein the intraocular pressure detection device further comprises a circuit board, the circuit board is received in the mounting groove, and the light-emitting assembly, the optical signal receiving assembly, and the processor are electrically connected to the circuit board.

* * * * *